US00PP25945P3

(12) United States Plant Patent
Olesen

(10) Patent No.: US PP25,945 P3
(45) Date of Patent: Sep. 29, 2015

(54) CLIMBING ROSE PLANT NAMED 'POULCY025'

(50) Latin Name: ***Rosa* hybrid**
Varietal Denomination: Poulcy025

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensburg (DK)

( * ) Notice: Subject to any disclaimer, the term of this patent is extended or adjusted under 35 U.S.C. 154(b) by 182 days.

(21) Appl. No.: 13/986,927

(22) Filed: Jun. 14, 2013

(65) Prior Publication Data

US 2014/0373202 P1 Dec. 18, 2014

(51) Int. Cl.
*A01H 5/00* (2006.01)

(52) U.S. Cl.
USPC ..... Plt./112

(58) Field of Classification Search
USPC ..... Plt./101, 109, 112
See application file for complete search history.

(56) References Cited

PUBLICATIONS

UPOV-Pluto Plant Variety Database International Union for the Protection of New Varieties of Plants, Jan. 19, 2015, obtained for cultivar name 'Poulcy025' (1 page total).*
Poulsen Roser A/S catalog; Retrieved from the Internet http://www.poulsenroser.com (1 page total).*

* cited by examiner

*Primary Examiner* — Susan McCormick Ewoldt

(57) ABSTRACT

A new garden rose plant of the Climbing class which has abundant, orange blend flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy025'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2005 and the resulting seeds were planted in a controlled environment in Fredensborg, Denmark. The new variety, named 'Poulcy025', originated as a single seedling from the stated cross.

The new variety may be distinguished from its male pollen parent and female seed parent primarily by growth habit. The female seed parent and the male pollen parents are both compact floribundas, while the claimed plant is a bushy climber.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance; and
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy025' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poulcy025' was selected in the spring of 2006 by the inventor as a single plant from the progeny of the aforementioned hybridization.

Asexual reproduction of 'Poulcy025' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poulcy025' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy025'. Specifically illustrated in the drawing are flowers at various stages of development, flower in parts, leaves, and stems. The age of illustrated plants is 2 years.

DETAILED DESCRIPTION OF THE VARIETY

The following is a description of 'Poulcy025', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulyc008', U.S. Plant Pat. No. 15,771 are compared to 'Poulcy025' in Chart 1.

CHART 1

| | 'Poulcy025' | 'Poulyc008' |
|---|---|---|
| Petal Count | 65 petals | 25 to 30 petals |
| Flower Diameter | 80 mm | 35 mm |
| General Tonality of Flower Color | Orange Group 27A with intonations of Red Group 38A. | Yellow-Orange Group 14C |

Flower and Flower Bud

Blooming habit: Continuous.

Flower bud:

*Size*.—Upon opening, 17 mm in length from base of receptacle to end of bud. Bud diameter is 15 mm.

*Bud form*.—Urceolate.

*Bud color*.—As sepals divide petals are Red Group 42A.

*Sepal inner surface*.—Color: Yellow-Green Group 146C. Surface: Smooth, moderately pubescent.

*Sepal outer surface*.—Color: Yellow-Green Group 144A with strong anthocyanin the color of Greyed-Red Group 180A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—15 mm long by 8 mm wide.

*Receptacle*.—Texture: Smooth. Size: 10 mm in height by 8 mm wide. Color: Yellow-Green Group 146B with strong anthocyanic pigments the color of Greyed-Purple Group 187B. Shape: Elliptical.

*Pedicel*.—Surface: Smooth. Length: 30 to 45 mm. Diameter: 2 mm on average. Color: Yellow-Green Group N144A with strong anthocyanic pigments the color of Greyed-Red Group 180A. Strength: Moderate.

*Peduncle*.—Length: 2 to 6 cm. Texture: Smooth. Diameter: 3 mm. Color: Yellow-Green Group N144A with strong anthocyanic pigments the color of Greyed-Red Group 180A.

Flower bud development: Flower buds are borne in clusters of 15 to 20 flower buds per stem, resembling a panicle. Reduced apical dominance in flower habit causes flower buds to develop relatively evenly from the base of the plant to the upper branches.

Flower bloom:

*Fragrance*.—Moderate floral, fruity scent.

*Duration*.—The blooms have a duration on the plant of approximately 10 to 15 days. Petals fall cleanly away from plant after flowers have fully matured.

*Size*.—Flower diameter is 80 mm when open. Flower depth is 40 mm.

*Flower shape*.—Open cup, double flower, with petals that curve out from the center.

*Shape of flower, side view*.—The upper portion is a flattened convex. The lower portion is deep concave.

Petalage: Under normal conditions, flowers have 65 petals total, 15 of which are petaloids.

General tonality of flower: Orange Group 27A with intonations of Red Group 38A. Tonality changes to Orange Group 36C Red Group 49A blend as the flower ages.

Petal color:

*Upon opening, inner and outer petals*.—Upper surface: Yellow-Orange Group 22C with shades of Yellow-Orange Group 14C at the petal base. Lower surface: Red Group 41C with intonations of Orange Group 24C at the margins.

*Basal petal spots, upon opening*.—Upper surface: Yellow Group 8A. Lower surface: Yellow Group 10B.

*After opening, outer petals*.—Upper surface: Yellow-Orange Group 22C with shades of Yellow-Orange Group 14C at the petal base. Lower surface: Red Group 41C and Red Group 49A blend. Orange Group 24C at the margins.

*After opening, inner petals*.—Upper surface: Yellow-Orange Group 22C with shades of Yellow-Orange Group 14C at the petal base. Lower surface: Red Group 41C and Red Group 49A blend. Orange Group 24C at the margins.

*Basal petal spots, after opening*.—Upper surface: Yellow Group 8A. Lower surface: Yellow Group 10B.

Petals:

*Petal reflex*.—Somewhat reflexed.

*Margin*.—Entire and uniform. Medium undulations of margin observed.

*Shape*.—Generally narrow elliptic. Apex shape: Rounded. Base shape: Acute.

*Size*.—40 mm (l)×35 mm (w).

*Texture*.—Smooth.

*Thickness*.—Average.

Petaloids:

*Size*.—24 mm (l) by 15 mm (w).

*Quantity*.—15.

*Shape*.—Symmetric, with a cleft at the center of the rounded apex. Base is acute.

*Color*.—Upper Yellow-Orange Group 19B splashed with Orange Group 28D. The lower side is Orange Group 29B.

Reproductive organs:

*Pollen*.—None observed.

*Anthers*.—Size: 2 mm in length. Color: Yellow Group 11B. Quantity: 35 on average.

*Filaments*.—Color: Yellow Group 13B. Length: 8 mm.

*Pistils*.—Length: 4 mm. Quantity: 20 on average.

*Stigmas*.—Color: Green-Yellow Group 1C.

*Styles*.—Color: Green-Yellow Group 1C.

*Location of stigmas*.—Inferior in location relative to the length of the filaments and the height of the anthers.

*Hips*.—None Observed.

Plant

Plant growth: Arching. Plants are 120 cm in height, and 100 cm wide.

Stems:

*Color*.—Juvenile growth: Yellow-Green Group 144C with anthocyanin the color of Greyed-Purple Group 183C. Mature growth: Yellow-Green Group 144B with anthocyanin the color of Greyed-Purple Group 183C.

*Length*.—On average, canes are 40 cm from the base of the plant to the flowering portion.

*Diameter*.—8 mm.

*Internodes*.—On mature canes, there is an average distance of 65 mm between nodes.

*Surface texture*.—Young wood: Smooth. Older wood: Smooth.

Long prickles:

*Incidence*.—13 prickles per 10 cm of stem.

*Size*.—Average length of prickles on mature stems is 11 mm.

*Shape*.—Upper and lower portion are concave.

*Color*.—Juvenile prickles: Greyed-Red Group 181A. Mature prickles: Greyed-Red Group 180A, 180B.

Plant foliage:

*Compound leaf*.—150 to 190 mm in length by 90 to 110 mm wide.

*Quantity*.—2 leaves per 10 cm of stem on average.

*Leaf bearing angle to the stem*.—45 degrees.

*Color of juvenile foliage*.—Upper side: Yellow-Green Group N144A. Lower side: Yellow-Green Group 144B. Anthocyanin: Greyed-Orange Group 173A.

*Color of mature foliage*.—Upper side: Yellow-Green Group 146A. Lower side: Yellow-Green Group 146B.

Plant leaves and leaflets:

*Stipules*.—Size: 16 mm in length. Quantity: 2 per compound leaf. Shape: Linear, slightly broad based with outward extending apecies. Margins: Finely serrated. Color: Yellow-Green Group 144A.

*Petiole*.—Length: 45 mm. Diameter: 1 mm.

*Upper surface*.—Color: Yellow-Green Group 144A with Greyed-Purple Group 183B.

*Lower surface*.—Color: Yellow-Green Group 144B. Observations: Small prickles observed.

*Rachis*.—Length: 50 mm. Upper surface: Color: Yellow-Green Group 144A with Greyed-Purple Group 183B.

*Lower surface*.—Color: Yellow-Green Group 144B. Observations: Small prickles observed.

*Leaflet*.—Quantity: Normal number of leaflets leaves in middle of the stem is 5 leaflets. Margins: Serrated. Size: Terminal leaflets on normal leaves are 45 to 60 mm in length by 34 to 43 mm wide. Shape: Generally ovate. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in The American Horticulture Society heat zone 7.

The invention claimed is:

1. A new and distinct variety of rose plant of the Climbing rose class named 'Poulcy025', substantially as illustrated and described herein, due to its abundant orange blend flowers, disease resistance, and extended period of bloom.

* * * * *

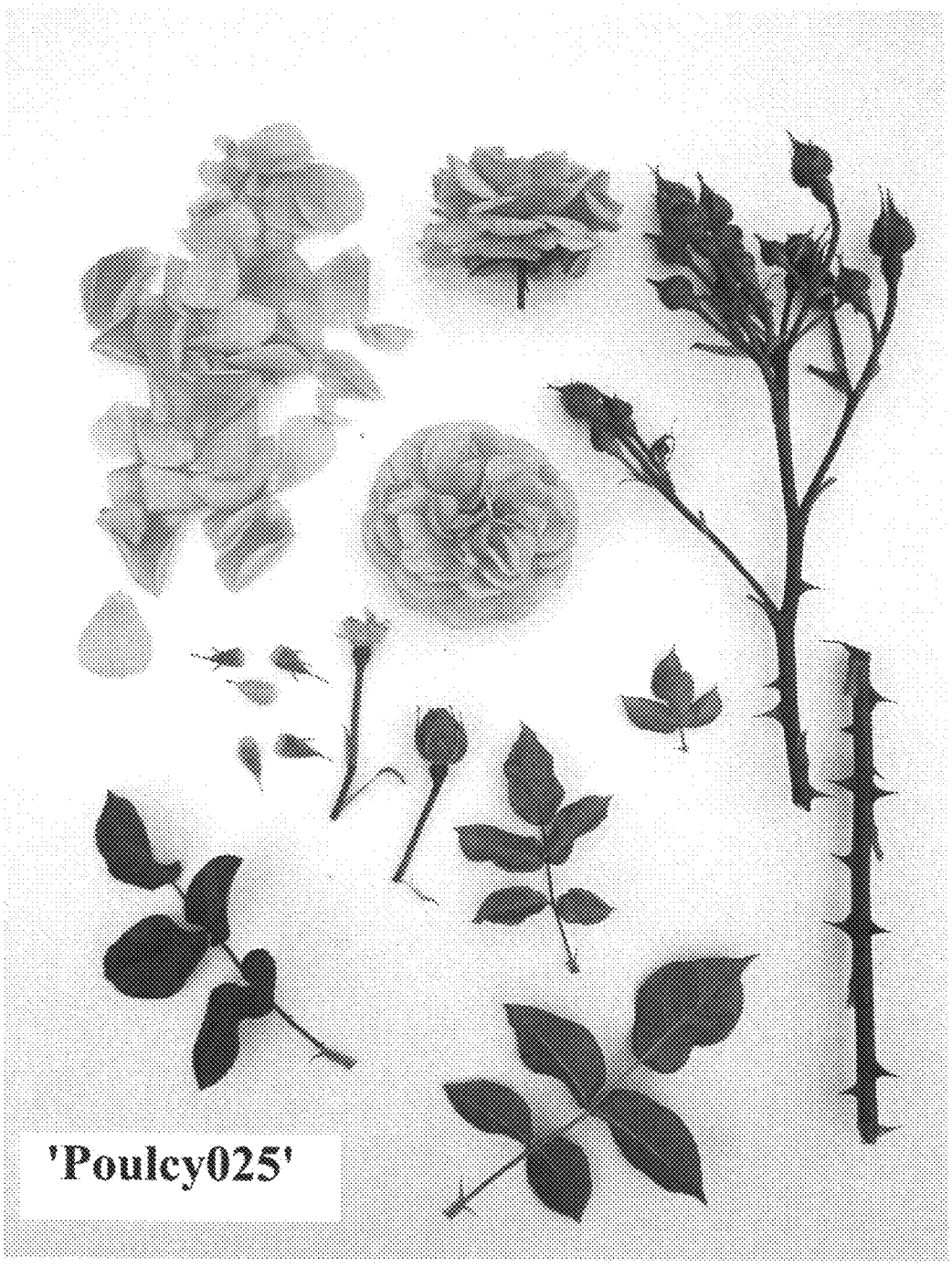
'Poulcy025'